US006315993B1

(12) United States Patent
Trampel

(10) Patent No.: US 6,315,993 B1
(45) Date of Patent: Nov. 13, 2001

(54) SERPULINA PILOSICOLI COMPETITIVE EXCLUSION PRODUCT

(75) Inventor: Darrell W. Trampel, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 09/335,109

(22) Filed: Jun. 17, 1999

Related U.S. Application Data

(63) Continuation-in-part of application No. 09/119,861, filed on Jul. 21, 1998, now abandoned.
(60) Provisional application No. 60/053,423, filed on Jul. 22, 1997, now abandoned.

(51) Int. Cl.$^7$ ................................................. A01N 63/00
(52) U.S. Cl. ...................................... 424/93.4; 435/252.1
(58) Field of Search ............................... 435/252.1, 822; 424/293.4

(56) References Cited

U.S. PATENT DOCUMENTS 5,750,118 * 5/1998 Vandeputte et al. ............... 424/262.1

OTHER PUBLICATIONS

Duenser, M. et al., Vienna Veterinary Monthy Journal, vol. 84(6), p. 151–161 (original and translation), Jul. 1997.*
Trivett–Moore, N.L. et al., J. of Clinical Microbiol., vol. 36(1), p. 261–265, Jan. 1998.*
Trott, D.J. et al., Infection & Immunity, vol. 64(11), p. 4648–4654, Nov. 1996.*
Atyeo, R.F. et al., FEMS Microbiology Letters, vol. 141, p. 77–81, Jul. 1996.*
Trott, D.J. et al., International J. of Systematic Bacteriology, vol. 48, p. 659–668, Jul. 1998.*
Thomson, J.R. et al., Infection & Immunity, vol. 65(9), p. 3693–3700, Sep. 1997.*
Emerging Technologies, Dec., 1997, PP 30 & 31, Doug Smith, Ph.D.
Aviguard Soluble Power, Sep. 30, 1996. Charles L. Hofacre.
Breaking Out of the Box, Jun./Jul., 1998, pp. 28–32, *Poultry Digest*.
New Product Reduces Salmonellae in Chickens, May 1, 1998, p. 1358, JAVMA, vol. 212, #9 .
Dateline NBC Nails the Egg Industry on Labeling; May, 1998, *Egg Industry* vol. 103(5), p–1 & 2.

*Feedstuff*, Mar. 23, 1998. vol. 70, No. 12, p. 1, 5.
Addressing Salmonellae Control with Biotechnology, Sep., 1997 K. E. Newman pp. 24–27, Poultry Digest.
Research Review, Jun./Jul., 1998—Poultry Digest, p. 4.
Undefined and Defined Bacterial Preparaitons for the Competitive Exclusion of Salmonella in Poultry, 1993; S. Stavric and J. Y. D'Aoust, J. Food Protection, 56:173–180.
CVM Update, Feb. 21, 1997—FDA, Center for Veterinary Medicine.
Reduction of Salmonella Crop and Cecal Colonization . . . , vol. 59, No. 7, 1996, pp. 638–693 by Michael E. Hume, Donald E. Corrier, David J. Nisbet and John E. DeLoach, J Food Protection.
Maintenance of the Biological Efficacy in Chicks . . . 1996, vol. 59, No. 12, pp. 1279–1283, J Food Protection, David Nisbet, Donald Corrier,Steven Ricke, M.E. Humbe, Allen Byrd & John DeLoach.
Poultry Science 1995; vol. 74, p. 1093–1101 Corrier,Nisbet, Scanlan,Hollister,Caldwell,Thomas,Hargis,Tomkins & DeLoach.
Salmonella Exclusion in Broiler Chicks . . . , Microbios 83 59–69, 1995.
Evaluation of the efficacy of Broilact®. . . 1992, *International Journal of Food Microbiology* 15(1992) 319–326.
Duenser, M. et al., Vienna Veterinary Monthy Journal, vol. 84(6), p. 151–161 (original and translation). Jul. 1997.
Trott, D.J. et al., Infection & Immunity, vol. 64(11), p. 4648–4654. Nov. 1996.
Atyeo, R.F. et al., FEMS Microbiology Letters, vol. 141, p. 77–81. Jul. 1996.
Trott, D.J. et al., International J. of Systematic Bacteriology, vol. 48, p. 659–668. Jul. 1998.
Thomson, J.R. et al., Infection & Immunity, vol. 65(9), p. 3693–3700. Sep. 1997.
Trivett–Moore, N.L. et al., J. of Clinical Microbiol., vol. 36(1), p. 261–265. Jan. 1998.

* cited by examiner

*Primary Examiner*—Irene Marx
(74) *Attorney, Agent, or Firm*—Zarley, McKee, Thomte, Voorhees & Sease

(57) ABSTRACT

A competitive exclusion product is described which includes a substantially pure culture of the bacterium species *Serpulina pilosicoli*, or a genetic equivalent thereof. When administered to an animal, the *S. pilosicoli* colonizes the cecal wall to prevent the colonization of other harmful bacteria, thereby preventing disease.

6 Claims, No Drawings

SERPULINA PILOSICOLI COMPETITIVE EXCLUSION PRODUCT

CROSS-REFERENCE TO A RELATED APPLICATION

This application is a continuation-in-part of commonly assigned provisional application Ser. No. 60/053,423, filed Jul. 22, 1997, now abandoned, and application Ser. No. 09/119,861, filed Jul. 21, 1998 now abandoned, the disclosures of which are hereby incorporated by reference.

BACKGROUND OF THE INVENTION

Microorganism populations in animal digestive systems are enormously complex biological ecosystems. Microorganisms normally inhabit the gastrointestinal tracts of human beings and other animals without invading the deeper tissues to cause disease. These microbes are consistently present in varying proportions. Their pattern of growth, conspicuously bacterial, is associated with the well-being of the animal and is necessary to its health.

Literally hundreds of species have been identified from animal intestinal tracts, and their populations can exceed 100 billion/g contents.

Typical residents of the gastrointestinal tract include coliforms, enterococci, Clostridium species, Proteus species, yeasts, Penicillium species, enteroviruses, *Pseudomonas aeruginosa*, aerobic and anaerobic streptococci, staphylococci, enterococci, *Alcaligenes faecalis*, Bacteroides species, and Lactobacillus species.

Microbial growth in the gastrointestinal tract is much more plentiful in the large intestine than the small intestine. The large intestine extends from the ileum to the anus and includes the cecum with vermiform appendix, colon, and rectum. The cecum is a blind pouch or cul-de-sac which forms the first portion of the large intestine. It is located below the entrance of the ileum at the ileocecal valve.

The age of the animal has a profound effect on intestinal physiology and microbial populations. Animals are born with a sterile intestinal tract and become colonized by those microbes in feed, or from their environment. Adult animals have a generally stable microflora that is usually disturbed only by drugs, disease, stress, or marked dietary changes.

The interaction between the animal, its environment, diet, and its residential microbial gut community is poorly understood. Inferences from the microbial balance have been made for the presence or absence of the disease state, and for reduced animal performance.

As an example, failure of chickens to reach expected levels of egg production is a problem frequently encountered in commercial egg-producing operations. Reduced egg production can be caused by a variety of viral, bacterial, toxic, and nutritional etiologies.

Commercial chickens in the United States and Europe have been reported to be infected with pathogenic intestinal spirochetes. In 1955, spirochetes were observed in cecal nodules of chickens, and these lesions were reproduced in chickens and turkeys by oral administration of infected cecal material. Mathey, W. J., et al. (1955), Spirochetes and cecal nodules in poultry. *J. Am. Vet. Med. Assoc.* 126:475–477. In 1986, it was reported that the isolation of a weakly hemolytic spirochete from the cecal mucosa of hens with diarrhea, chickens and swine from the same farm had a history of intermittent diarrhea. Davelaar, F. G., et al. (1986), Infectious typhlitis in chickens caused by spirochetes. *Avian Pathol.* 15:247–258. A subsequent fluorescent antibody microscopic study identified intestinal spirochetes in 27.6% of flocks with intestinal disorders and in 4.4% of flocks lacking signs of enteritis. Dwars, R. M., et al. (1989), Incidence of spirochetal infections in cases of intestinal disorders in chickens. *Avian Pathol.* 18:591–595. Retarded growth rates and delayed onset of egg production were associated with spirochete infection of pullets in Great Britain. Griffiths, I. B., et al. (1987), Retarded growth rate and delayed onset of egg production associated with spirochete infection in pullets. *Vet. Rec.* 121:35–37. The latter chickens were reared on deep litter and had indirect contact with swine. Further, pasty vents and dirty eggshells in Ohio laying hens shortly after molting were associated with cecal spirochetes. Swayne, D. E., et al. (1992), Association of cecal spirochetes with pasty vents and dirty eggshells in layers. *Avian Dis.* 36:776–781.

While the above reports indicated an association between cecal spirochetes and infection in chickens, the oral administration of human spirochetes to broiler chicks did not cause clinical signs of disease or gross lesions. Dwars, R. M., et al. (1992), Infection of broiler chicks (Gallus domesticus) with human intestinal spirochaetes. *Avian Pathol.* 21:559–568. However, inoculating avian intestinal spirochetes into the crop of hens resulted in wet droppings and invasion of spirochetes into and beneath cecal epithelium. Dwars, R. M., et al. (1990), Observations on avian intestinal spirochaetosis. *Vet. Q.* 12:51–55.

In 1993, it was determined that intestinal cecal spirochetes were a cause of reduced egg production during the early part of the first laying cycle. Trampel, D. W., et al. (1994), Cecal Spirochetosis in Commercial Laying Hens. *Avian Dis.* 38:895–898. In this study, affected chickens necropsied were found to have an orderly, dense, uniform layer of spirochetes covering the entire mucosal surface of the ceca. Id.

Current treatments for intestinal pathogens have included treatment with therapeutic drugs, such as antimicrobials, to eradicate or decrease the number of pathogens. However, if the animal is a domesticated livestock animal used for human food consumption, adulteration of the carcass with drugs is not desirable.

Other treatments for intestinal pathogens in poultry and other livestock have included the administration of competitive exclusion products. Direct feed microbials have been successfully used to replenish the gut bacterial population with natural beneficial bacteria. One such product, sold under the trade name Preempt®, contains 29 different species of bacteria. It is desirable to narrow the strains of the direct feed microbials to those minimum number of strains which are efficacious in order to decrease cost and to maximize benefit to the animal. In fact, one of the greatest difficulties with these direct feed treatments has been to find which strains from the wide consortium of bacteria, are truly effective in producing the desired result in animals, and especially livestock.

It has now been discovered that a single, defined bacterium is effective in reducing or eliminating diseases caused by undesirable microbes which colonize the ceca of animals. The bacteria corrects the pathology of the animal's system in such a manner that the host animal is quickly returned to an economically producing animal.

Accordingly, it is a primary objective of the present invention to provide a competitive exclusion product to provide a method of enhancing the overall well-being of poultry by use of a single, defined bacterium.

It is a further objective of the present invention to provide a competitive exclusion product which, when fed, corrects the pathology of the animal system in such a manner that the host animal is quickly returned to an economically producing animal.

It is another objective of the present invention to provide a competitive exclusion product in the form of a direct-fed microbial composition which can be fed in conjunction with daily free choice feed rations.

It is yet another objective of the present invention to provide a competitive exclusion product which can be fed to poultry in order to increase overall health, well being, and in general, increase the economics of the animal to its producer.

It is still a further objective of the present invention to provide a competitive exclusion product which contains only one, defined bacterium, and therefore does not contain extraneous, costly and unnecessary strains of bacteria.

It is another objective of the present invention to provide a competitive exclusion product which is safe and economical to administer to the animal.

The method and means of accomplishing each of the above objectives as well as others will become apparent from the detailed description of the invention which follows hereafter.

SUMMARY OF THE INVENTION

The invention describes a method and means for eradicating or decreasing the number of disease-causing microbes in the intestinal tract of poultry. The invention has been found to be especially effective in treating cecal spirochetosis in poultry. The treatment involves the administration of the single bacterium *Serpulina pilosicoli,* or the genetic equivalents thereof. The preferred strain of *Serpulina pilosicoli* is laboratory strain 42167 (*S. pilosicoli* 42167). The bacteria are administered orally in conjunction with feed or water rations. Following administration, the bacteria colonize the ceca to the extent that other harmful bacteria, such as Salmonella and Camphylobacter, are prevented from attaching to the cecal wall.

DETAILED DESCRIPTION OF THE PREFERRED EMBODIMENT

As earlier described, the invention herein relates to administering to poultry for a period of time a small, but disease-preventing effective amount of a competitive exclusion product. The product includes the spiral-shaped bacterium Serpulina pilosicoli, or the genetic equivalent thereof. The preferred bacteria strain is *S. pilosicoli* 42167.

The term "genetic equivalent" as used herein is to be understood to mean not only the precise species *Serpulina pilosicoli,* but mutants thereof, or genetically altered bacteria which nevertheless have a common identifying characteristic of successful performance in the present invention.

This invention has been found to be particularly effective in poultry, which is intended to include domestic poultry, such as chickens, turkeys, and ducks. Chickens are inclusive of broiler (meat-type) chickens and leghorn (egg-type) chickens.

From time to time, reference is made to a biologically pure or substantially pure culture of the above referred to bacteria species. This is intended to refer to a culture which contains no other bacterial species in quantities sufficient that they interfere with the effectiveness of the *S. pilosicoli.* It is important that cultures be substantially free of interfering bacteria, since other bacteria either have no effect or may have a detrimental effect on achieving the objectives of the invention.

Further, the *Serpulina pilosicoli* bacteria of this invention are substantially live, non-pathogenic organisms. "Substantially live, substantially non-pathogenic organisms" is herein defined as organisms which contain an insufficient amount of dead or disease-producing organisms to interfere with the effectiveness of the bacteria. *S. pilosicoli* 42167 is an example of a strain of Serpulina pilosicoli that is substantially non-pathogenic.

*Serpulina pilosicoli* is easily diagnosed microscopically, but has been identified only during the last few years, and received a scientific name only about two years ago. The finding of this organism in chickens is rare. There is no evidence suggesting that *Serpulina pilosicoli* is part of the normal intestinal flora of chickens.

Generally speaking, the bacteria described herein should be administered in a preventative manner before disease, but certainly as soon as disease is noted. A preferred method is to administer a single dose of the bacteria within the first week of life of the animal, and most preferably during the first day of life. The bacteria can be given to the animal through its water or feed. The bacteria may also be administered with other non-toxic carriers in the form of an injection, oral innoculation, or intravenous administration. Such non-toxic carriers are well known in the art and include water, saline, and non-toxic vegetable oil.

Following administration, the bacteria colonize the cecum of the animal. The colonization of the bacteria is so extensive on the wall of the cecum that other undesirable bacteria, such as Salmonella and spirochetes, cannot attach to the cecal wall themselves. Thus, the undesirable bacteria cannot invade the animal's body and cause disease.

The level of the organism count should be within the range of $10^1$ organisms to about $10^9$ organisms/gram of diet, preferably from about $10^2$ to about $10^4$ organisms/gram of diet. The diet can then be administered to the animals ad libium or on a scheduled basis.

The manner of administering the bacteria may be by conventional mixing with feed or water. The feed or water is thereafter fed in a free choice manner.

The present invention offers the advantages of providing a singular source of bacteria, a spirochete, which is more effective in coating the inner surface of the cecal wall than other known competitive exclusion products. This dense, uniform coating of *S. pilosicoli* prevents other disease-causing bacteria, such as other strains of spirochetes, Salmonella, and Campylobacter, from attaching to the cecal wall. Since the competitive exclusion product of the present invention includes only the single bacterium *S. pilosicoli,* it is easier and less expensive to mass produce. Further, it is easier to monitor in treated birds.

The following examples are offered to illustrate but not limit the invention. Thus, they are presented with the understanding that various formulation modifications as well as method of delivery modifications may be made and still be within the spirit of the invention.

EXAMPLE 1

Pathogenicity of a Chicken Strain of *Serpulinapilosicoli*

Materials and Methods 20 pathogen-free, white leghorn chicks were used in the experiment. Ten were used as controls and ten were administered *S. pilosicoli* 42167 in their feed. The two groups of chicks were kept in separate brooder units.

The use of specific pathogen free (SPF) chickens, as in this experiment, is standard procedure throughout the United States. Research involving microorganisms and chickens should always be done in SPF chickens so that one can be reasonably sure that observations can be attributed to the experimental microorganism administered. Other chickens (non-SPF) may already possess microorganisms that would invalidate the experimental results.

The control and *S. pilosicoli* groups were inoculated 2 days posthatch. The control group was inoculated with BHIS medium and the *S. pilosicoli* group was given spirochetes in a concentration of $10^8$ spirochetes/ml. The inoculations were in 0.5 ml increments via crop gavage. Three inoculations were administered at 4 hour intervals.

Parameters Measured

The chicks were observed for the following parameters in the following frequencies:

| Observation | Frequency |
| --- | --- |
| Clinical signs | daily |
| Body weights | weekly |
| Cloacal cultures | weekly |
| Excreta dry matter | 3 weeks PI |
| Excreta fat content | 3 weeks PI |
| Pathology | 3 weeks PI |
| ELISA titers | 3 weeks PI |

Results and Discussion

TABLE 1

Cloacal Isolation of *Serpulina pilosicoli*

| | Days Postinoculation | | | |
| --- | --- | --- | --- | --- |
| Group | −1 | 7 | 14 | 21 |
| Control | 0 | 0 | 0 | 0 |
| *S. pilosicoli* | 0 | 5 | 4 | 8 |

TABLE 2

Cecal Colonization (21 days PI)

| Extent | Controls | *S. pilosicoli* |
| --- | --- | --- |
| Slight | 0 | 3 |
| Moderate | 0 | 0 |
| Heavy | 0 | 7 |

As shown above, Tables 1 and 2 demonstrate that ceca of chickens become colonized by *S. pilosicoli* upon oral exposure.

TABLE 3

ELISA Serology

| Group | Titer |
| --- | --- |
| Control | 0.052 |
| *S. pilosicoli* | 0.144* |

*$P \leq 0.005$

Neither group showed any clinical signs of diarrhea or depression.

Table 3 demonstrates that chickens develop an immune response to *S. pilosicoli*.

TABLE 4

Mean Body Weights

| | Days Postinoculation | | | |
| --- | --- | --- | --- | --- |
| Group | −1 | 7 | 14 | 21 |
| Control | 34.7 | 57.6 | 119.2 | 169.9 |
| *S. pilosicoli* | 34.4 | 51.1 | 132.5 | 194.3 |

Table 4 demonstrates that chickens inoculated with *S. pilosicoli* gain weight faster than chickens that are not inoculated.

TABLE 5

Dry Matter Content of Excreta (% of Weight)

| | Days Postinoculation | | |
| --- | --- | --- | --- |
| Group | 7 | 14 | 21 |
| Control | 51.1 | 48.9 | 45.8 |
| S. pilosicoli | 58.4 | 50.5 | 41.4 |

Table 5 demonstrates that chickens inoculated with *S. pilosicoli* do not develop diarrhea. Dry-matter content of feces was not significantly different from the control.

TABLE 6

Fat Content of Excreta (% of Dry Matter)

| | Days Postinoculation | | |
| --- | --- | --- | --- |
| Group | 7 | 14 | 21 |
| Control | 1.20 | 1.35 | 1.10 |
| S. pilosicoli | 1.72 | 1.16 | 1.11 |

Table 6 demonstrates that absorption of fat is not different between the *S. pilosicoli*-inoculated chickens and the control group.

Conclusions

The study demonstrates that *Serpulina pilosicoli* readily colonizes the ceca of 2-day-old chicks. The chicks infected with a chicken strain of *S. pilosicoli* were asymptomatic. The end-on-attachment of the bacteria is via indentation of apical enterocyte cell membranes. Antibodies can be detected by ELISA by 21 days following oral exposure.

Not only was the *Serpulina pilosicoli* bacteria nonpathogenic, but it was also beneficial. As shown above, the inoculated chickens gained weight faster than the control birds.

As shown above, the competitive exclusion product of the present invention antimicrobial composition of the present invention is effective in colonizing the cecal wall of poultry. It also prevents other harmful bacteria from attaching to the animal's cecal wall, thereby reducing diarrhea and other diseases in the animal and further increasing the animal's productivity. The use of a competitive exclusion product containing only one bacterium offers the advantages of being less expensive to produce in large quantities and, in addition, makes it easier for the caregiver to monitor the treated birds. It is therefore submitted that the present invention accomplishes at least all of its stated objectives.

Deposits

A deposit of *S. pilosicoli* 42167 is and has been maintained by the inventor since prior to the filing date of this application. Access to this deposit will be available during the pendency of the application to the Commissioner of Patents and Trademarks and persons determined by the Commissioner to be entitled thereto upon request. Upon allowance of any claims in the application, the Applicant will make available to the public without restriction a deposit with the American Type Culture Collection (ATCC), 10801 University Boulevard, Manassas, Va. 20110—2209. The organisms deposited with the ATCC will be taken from the same deposit maintained by the inventor and described above. Additionally, Applicant will meet all the requirements of 37 C.F.R. §1.801–1.809, including providing an indication of the viability of the sample when the deposit is made. this deposit of S. pilosicoli 42167 will be maintained in the ATCC Depository, which is a public depository, for a period of 30 years, or 5 years after the most recent request, or for the enforceable life of the patent, whichever is longer, and will be replaced if it ever becomes nonviable during that period. Applicant will impose no restrictions on the availability of the deposited material from the ATCC; however, Applicant has no authority to waive any restrictions imposed by law on the transfer of biological material or its transportation in commerce. Applicant does not waive any infringement of its rights granted under this patent.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

I claim:

1. A method of manufacturing a composition useful for colonizing the intestinal tract of an animnal that is a member of the poultry group comprising:

combining an amount of a live, biologically pure culture of *Serpulina pilosicoli* 42167 effective for colonizing the intestinal tract of poultry with a non-toxic carrier.

2. A composition for poultry useful for colonizing the intestinal tract of poultry comprising:

an amount of a live, biologically pure culture of *Serpulina pilosicoli* 42167 effective for colonizing the intestinal tract of poultry; and poultry feed or water.

3. A composition for administration to an animal that is a member of the poultry group to prevent disease-causing microbes from colonizing the intestinal tract of the animal comprising:

an amount of a live, biologically pure culture of *Serpulina pilosicoli* 42167 effective for colonizing the intestinal tract of poultry; and a non-toxic carrier.

4. The composition according to claim 3 further including feed or water of the animal, whereby said culture is admixed with the feed or water.

5. The composition according to claim 3 wherein the culture is present in a concentration of from about $10^1$ to $10^9$ organisms per gram of animal diet.

6. The composition according to claim 3 wherein the animal is a chicken.

* * * * *